United States Patent [19]

Chang et al.

[11] Patent Number: 4,499,901
[45] Date of Patent: Feb. 19, 1985

[54] RETREATED SENSING ELECTRODE

[75] Inventors: Joseph J. Chang; Maynard Ramsey, III, both of Tampa, Fla.

[73] Assignee: Critikon, Inc., Tampa, Fla.

[21] Appl. No.: 509,500

[22] Filed: Jun. 30, 1983

[51] Int. Cl.³ ............................................ G01N 27/30
[52] U.S. Cl. ................................... 128/635; 204/402; 204/415
[58] Field of Search .............. 128/635, 642, 632; 204/415, 403, 402, 1 P, 1 Y, 416; 422/24

[56] References Cited

U.S. PATENT DOCUMENTS

| | | | |
|---|---|---|---|
| 3,468,303 | 9/1969 | Mosier | 128/839 |
| 3,826,678 | 7/1974 | Hoffman et al. | 117/81 |
| 3,912,614 | 10/1975 | Spracklen et al. | 204/415 |
| 3,918,099 | 11/1975 | Führ et al. | 106/124 X |
| 3,966,580 | 6/1976 | Janata et al. | 204/415 X |
| 4,033,357 | 7/1977 | Helland et al. | 128/419 P X |
| 4,081,334 | 3/1978 | Suzuki et al. | 204/1 T |
| 4,240,889 | 12/1980 | Yoda et al. | 204/403 |
| 4,276,144 | 6/1981 | Hahn et al. | 204/415 |
| 4,317,879 | 3/1982 | Busby et al. | 204/416 X |
| 4,340,457 | 7/1982 | Kater et al. | 204/415 |

OTHER PUBLICATIONS

Barr et al., "The Development of Chronic Insertable Electrodes", U.S. Dept. of Commerce Nat. Tech. Inf. Ser., 9/1975.
Edwin G. Brown, "Appl. To Animals and Humans of Cont. Mon. Oxygen Sys.", U.S. Dept. of Commerce, N.T.I.S., pp. 276-448, 6/1976.
E. G. Brown, "Development of Clinical Evaluation of Blood Gas Sensors for Cont. Mon. (Adult and Neonate)", U.S. Dept. of Commerce, N.T.I.S., P258798, 6/1976.
R. E. Baier, "The Organization of Blood Components Near Interfaces", Annals of the New York Academy of Sciences, vol. 283, The Behavior of Blood and its Components at Interfaces, pp. 17-36, NY, NY, 1977.
Kogawa et al., "Blood Elements at Foreign Surfaces: A Biochemical Approach to the Study of the Adsorption of Plasma Proteins", Annals of the New York Academy of Sciences, vol. 283, The Behavior of Blood and its Components at Interfaces, pp. 37-48, NY, NY, 1977.
Vroman et al., "Reactions of Formed Elements of Blood with Plasma Proteins at Interfaces", Annals of New York Academy of Sciences, vol. 283, The Behavior of Blood and its Components at Interfaces, pp. 65-74, NY, NY, 1977.
Cuypers et al., "Ellipsometric Study of Protein Film on Chromium", annal of the New York Academy of Science, vol. 283, The Behavior of Blood and Its Components at Interfaces, pp. 77-84, NY, NY, 1977.
Salzman et al., "Surface Induced Platelet Adhesion, Aggregation and Release", Annals of the New York Academy of Science, vol. 283, The Behavior of Blood and its Components at Interface, pp. 114-125, NY, NY, 1977.
Hoffman et al., "Interactions of Blood and Blood Components at Hydrogels Interfaces", Annals of the New York Academy of Sciences, vol. 283, The Behavior of Blood and its Components at Interfaces, pp. 372-381, NY, NY, 1977.
Ma et al., "Organic Analysis Using Ion-Selective Electrodes", vol. 1, Method; p. 47, 1982, London, England.
Lindon et al., "MIT Industrial Liaison Program; In Vivo Assessment of Throboresistant Materials by Determination of Platelet Survival", Jun. 18, 1981, MIT Department of Chem. E.
Hoffman et al., "Covalent Binding of Biomolecules to Radiation-Grafted Hydrogels on Inert Polymer Surfaces", vol. XVIII, Trans. Amer. Soc. Artf. Int. Organs, 1972.

(List continued on next page.)

Primary Examiner—G. L. Kaplan
Assistant Examiner—Nam X. Nguyen
Attorney, Agent, or Firm—Jason Lipow

[57] ABSTRACT

An improved sensing electrode assembly for testing for a constituent in blood is provided. An electrode assembly exhibits a decreased time to reach stable operation by virtue of having the assembly pretreated by applying thereto a liquid containing blood derived albumin.

15 Claims, 4 Drawing Figures

OTHER PUBLICATIONS

Barr et al., "Development of Chronic Insertable, Oxygen Electrodes", University of Missouri, 7/79.

The Veterans Administration Hospital Interface Lab., Brooklyn, NY, Contract PH 43-66-79, Fourth Annual Contractors Conference, Jan. 1971, "The Effect of Human Blood Plasma and Serum on Pre-Adsorbed Protein Films".

Holly et al., "Water Wettability of Proteins Adsorbed at Hydrogel-Water Interface", ACS Symposium series 31, Hydrogels for Medical and Related Applications, J. D. Andrade, 1976, Wash. D.C.

Kim et al., "Competitive Ads. of Plasma Porteins onto Polymer Surface", Bio. Appl. of Polymer, vol. 17, pp. 69-74, NY, NY, 1975.

Shichiri et al., "Wearable Art. Endrocrine Pancreas with Needle-Type Glucose Sensor", The Lancet, pp. 1129-1131, 11/82, London, England.

RETREATED SENSING ELECTRODE

BACKGROUND OF THE INVENTION

This invention relates to electrochemical analysis commonly referred to as amperometric analysis or alternatively as polarographic analysis. Specifically, this invention relates to an electrode assembly designed to perform as a sensor for monitoring the concentration of selected components in blood and is particularly applicable to such a sensor when used for the in vivo monitoring of blood gas concentrations, e.g., oxygen tension in blood vessels of living animals including humans.

In U.S. Pat. No. 3,912,614 issued on Oct. 14, 1975 to S. B. Spracklen and H. Watanabe Capistrano, a sensing electrode assembly for incorporation into a sensor has been described. Briefly, the electrode assembly comprises a fine gauge electrode composed of a noble metal which is covered by a selectively permeable membrane. The sensing electrode is immersed into the stream to be tested, e.g., into the blood vessel of a living animal and is polarized. In the case of measuring oxygen tension in blood, for example, oxygen in the blood tends to diffuse through the membrane to the electrode where the oxygen is reduced by reacting with water in the blood and accepting electrons from the electrode to form hydroxyl ions. Where the electrode is made part of a closed electrical circuit including, for example, a reference electrode, connecting electrical wiring, means for imposing a potential at the sensing electrode and means for detecting current flow, the flow of the electrons from the sensing electrode constitute a current flow through the electrical circuit and the amperage of that current flow is directly related to the oxygen tension in the blood stream.

As has been described in the aforementioned U.S. Pat. No. 3,912,614 as well as in U.S. Pat. No. 3,757,771 issued to F. A. Ruegg, et al. on Sept. 11, 1973; such a device has been employed in monitoring changes in blood oxygen in living animals, including humans. In particular, it is useful for the continuous monitoring of such blood oxygen tension in the case where conventional blood analysis is impractical. Such a circumstance exists in the case of new born infants and especially, for prematurely born infants where, because of the relatively small quantity of total blood present in the body of such infants, it is impractical and dangerous to frequently extract blood samples for in vitro testing using conventional methods. Instead, the use of a continuous in vivo monitoring system, as is described herein, is a far more preferable alternative.

Ideally, the sensor electrode is inserted into the blood vessel of the living animal and by use of an amperage sensing meter, calibrated to read directly in partial pressure of oxygen, the oxygen blood level in that vessel can be immediately and continuously monitored.

Unfortunately, the sensing devices heretofore utilized have fallen short of this ideal situation. It has been experienced that when the sensing electrode is first introduced into a blood vessel, the initial reading is relatively high. Thereafter, notwithstanding the fact that the blood oxygen tension remains constant, the reading begins to decrease, first at a rapid rate and then at a decreasing rate. It is only after the passage of a relatively long time period, e.g., six hours, that the rate of decrease becomes relatively low enough so as to provide a reliable base line for measuring significant changes in blood oxygen tension.

This time period for allowing the sensor to reach a stable, reliable state of operation is intolerably long in many of the potential uses for the sensor where the first few hours of monitoring are critical to the patient's welfare. Accordingly, there is a need for decreasing this time period.

SUMMARY OF THE INVENTION

In accordance with the teachings of this invention, an improved sensing electrode assembly for testing for a constituent in blood, such as for example, oxygen tension, is provided. The electrode assembly is of the type including an electrode, a supporting structure for the electrode, and a selectively permeable membrane covering the electrode.

It has been discovered that if the electrode has been pretreated by having applied to the covering membrane a solution comprising blood derived albumin, the electrode may be employed immediately and will reach a reliable stable operating condition in a significantly decreased time period, as contrasted to untreated electrodes. While a variety of albumin containing solutions may be applied to the membrane, it is particularly effective to employ human blood serum.

The application of the solution is preferably for an extended period of time varying from 10 minutes to 6 hours with between 1 hour to 3 hours being preferable. This may be accomplished by simply immersing the membrane covered electrode in the solution and holding it there for the desired time interval. The so treated electrode may thereafter be dried and sterilized without losing the benefit of the pretreatment step. In a preferred embodiment the dried treated electrode may be coated with a liquid silicon composition to preserve the treatment as well as facilitate the insertion of the electrode into a blood vessel.

DETAILED DESCRIPTION OF THE INVENTION

Figure 1:
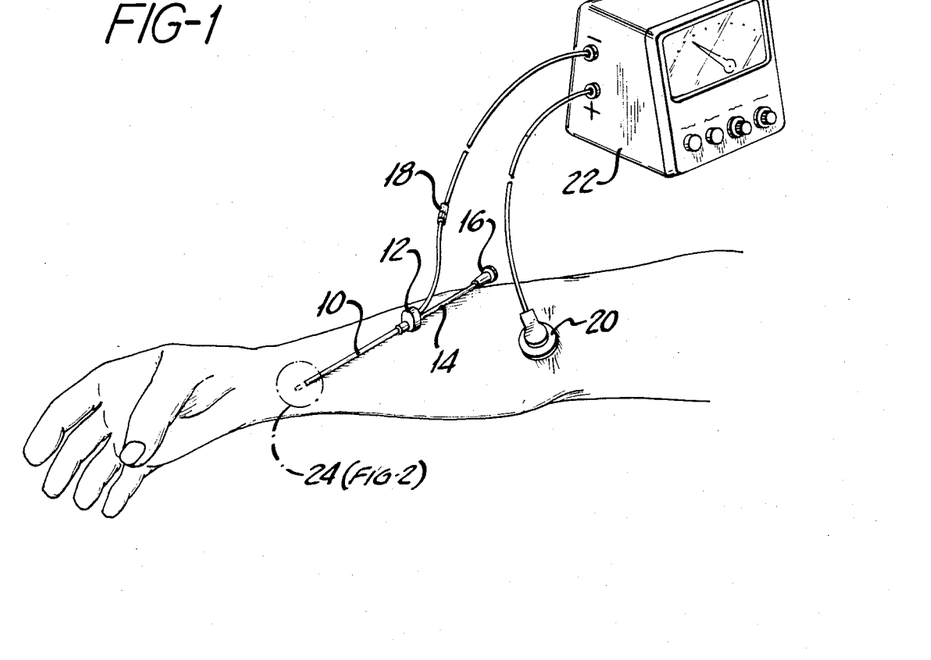
FIG. 1 is a schematic diagram illustrating the employment of a sensor incorporating the teachings of this invention in monitoring blood oxygen concentrations in a living human blood vessel.

Referring now to FIG. 1, schematically illustrated therein is a sensor utilizing the pretreated electrode of this invention to monitor the blood oxygen content in a human arm. The sensing electrode is contained in a first lumen of a flexible tube 10 which tube is provided with a second lumen, employed for withdrawing blood samples, for pressure monitoring, and for infusion of liquids, e.g., for flushing or medication. The second lumen is provided with a sidepoint 29 for flow communication with the blood vessel. A Y-coupling 12 is provided at the distal end of tube 10 where the sampling lumen is in flow communication with the sampling tube 14 which terminates in sampling hub 16. Sampling hub 16 is adopted to be connected to sampling and liquid infusion means which are not shown. The electrode lumen of tube 10 also terminates at its distal end at Y-coupling 12 and is electrically connected to electrical connecter 18. Also electrically connected to connecter 18 is reference electrode 20 and the instrument 22. In this manner an electrical circuit is completed through which the current induced by the reaction between blood oxygen and the sensing electrode flows and is measured by the instrument 22. The current, being proportional to the oxygen tension in the blood stream can therefore be monitored, by instrument 22 on a dial read either directly in nanoamperes or calibrated to read in partial pressure of oxygen in mm. of Hg.

Figure 2:
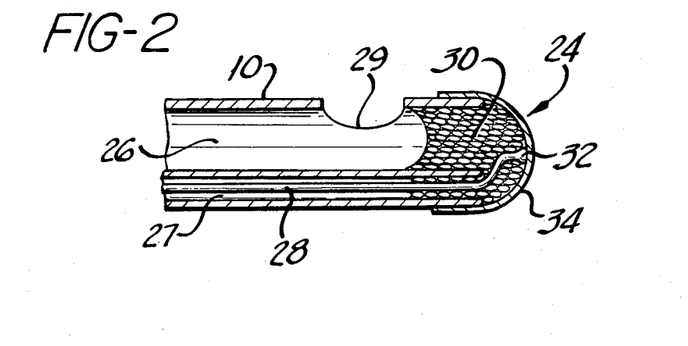
FIG. 2 is a longitudinal cross sectional view of the proximal end of the sensing electrode in the sensor of FIG. 1.

Referring now to FIG. 2, illustrated therein enlarged longitudinal cross-section, is the proximal end of the sensing electrode 24. As described, tube 10 comprises two lumens; a sampling lumen 26 and an electrode wire lumen 27. Tube 10 may be constructed of any suitable, flexible material having sufficient strength and safety characteristics to be employed in the medical device being considered herein. The material of choice is polyvinyl chloride.

Contained within the electrode wire lumen 27 is a metal electrode wire 28 which, in the preferred embodiment is essentially pure silver. It will be understood that a wide variety of other metals may be employed as the electrode wire including, for example, the noble metals such as platinum, palladium, gold and the like. The electrode wire 28 is encased at the proximal end of tube 10 in an electrically insulating material 30 such as for example, epoxy resin.

The extreme tip 32 of the encased electrode wire is exposed from the encasing epoxy resin by grinding away the resin at the tip of the electrode.

As is taught in U.S. Pat. No. 3,912,614, the proximal end of the electrode is then coated with a membrane material 34. The membrane is chosen to prevent direct contact between the main blood stream and the electrode and to permit selected constituents of the blood stream, e.g., oxygen, to migrate through the membrane for electrochemical reaction at the electrode.

Preferably the membrane comprises a lightly cross linked hydrophilic polymer of the kind set out in detail in U.S. Pat. No. 3,912,614, which description is incorporated herein by reference. Typical of such suitable materials is the polymer sold under the trademark Hydron by Smith and Nephew Associated Companies Ltd. in England and by National Patent Development Corporation in the United States. The polymer, polyhydroxyethyl methacrylate is available as a powder which is soluble in an alcoholic solution. In a preferred method of manufacture, the linear polymer, dissolved in methyl alcohol, is combined with a cross linking agent such as for example an aqueous solution of $(NH_4)_2Cr_2O_7$. The tip of the epoxy resin encased electrode is dipped into the solution to deposit a coating thereon. A plurality of coating steps may be employed. The coated tip is then further cured by submitting it to additional cross linking steps. For example, the tip may then be subjected to ultraviolet irradiation as well as to a heating step.

In general, the dimensions of the electrode 24 and its various components are selected to be suitable for the particular use for which it is to be employed. Typically, for a sensor to be used to monitor blood gas concentration a relatively small tube 10 is required which may range generally from about 0.3 to about 2 mm. in outside diameter. The membrane, at the tip, generally is applied in the shape of a hemisphere having the same diameter as the tube 10 and is applied in a thickness, measured from the tip 32 of the electrode wire 28, of about 0.005 to about 0.05 mm.

The gauge of the electrode wire should be carefully chosen to suit the purpose for which the sensor is to be used. The extent of electrochemical reaction and hence the magnitude of the current generated are proportional to the area of contact between the liquid and the electrode. It is therefore important that the exposed electrode and hence the gauge of the wire be large enough to produce sufficient reaction to generate a measurable current. On the other hand, the effect of too large an area of contact and hence too extensive a reaction is to deplete the electrode-liquid interface of oxygen and instead develop an oxygen gradient between the electrode and the main stream of the liquid to be measured. Such a gradient distorts the relationship between the measured concentration and the actual concentration in the main stream and creates intolerable lags in monitoring concentration changes.

For the case of measuring oxygen concentration in a blood stream, a usable wire gauge of from about 0.05 to about 0.5 mm. may be employed.

To ease in application, it is preferred that the electrode be fully coated with a medical grade silicone oil.

In accordance with the teachings of this invention, it has been discovered that electrodes incorporated into sensors of the kind heretofore described have suffered from the inability to reliably stabilize within a tolerable time period when employed in measuring blood gas in live animals. This shortcoming is particularly surprising in view of the contrasting performance of such sensors under in vitro conditions wherein stability is achieved almost instantly.

Figure 3:
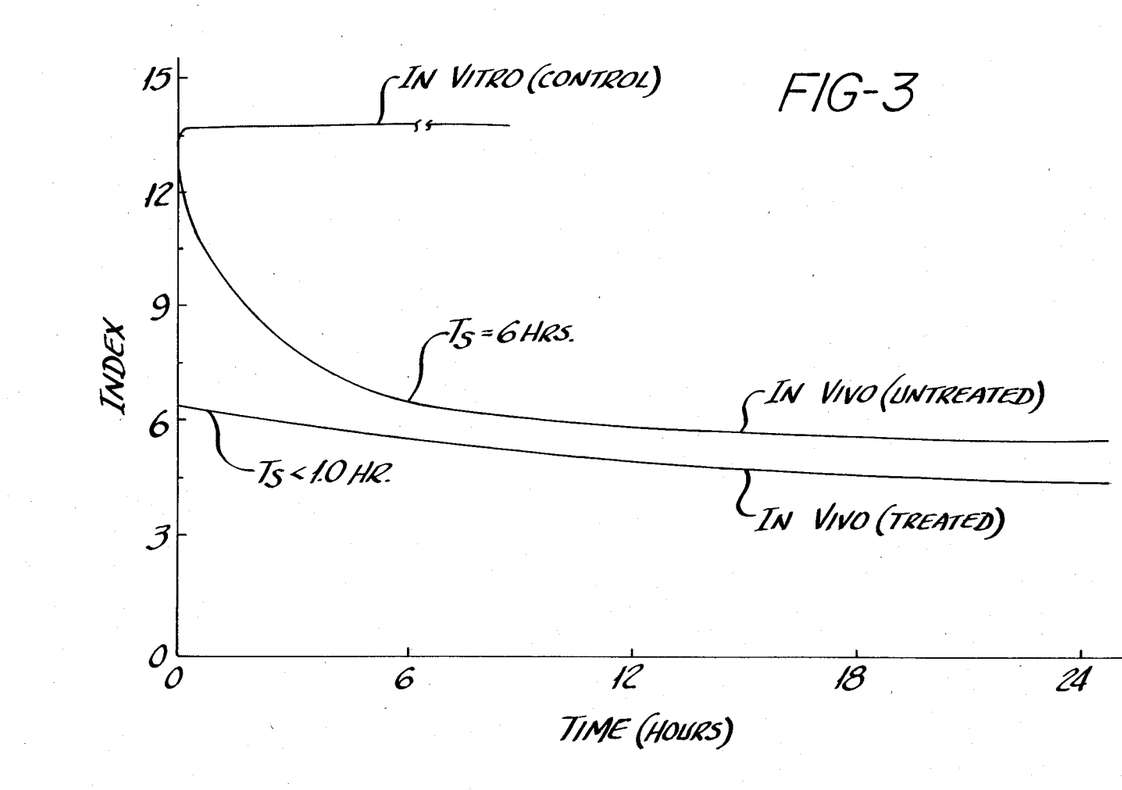
FIG. 3 is a graphical representation of the stabilization time of treated and untreated electrodes both in vivo and in vitro.

To illustrate the anomalous performance of the prior sensors, reference is made to FIG. 3 which is a plot of the performance of various sensors under both in vitro and in vivo conditions.

The abscissa of this plot is time, measured in units of hours with the origin, time zero, being the point at which the sensor, and more particularly, the sensing electrode, is first introduced into the liquid stream. The ordinate of this plot is the Index which is the ratio of the measured current reported by the instrument 22 (see FIG. 1) in nanoamperes (nA) divided by the actual partial pressure of the measured component in the liquid stream in mm of Hg. For the purposes of this discussion, the measured component will be exemplified by the partial pressure of oxygen in the liquid stream. This actual concentration is determined by noncontinuous, conventional instrumentation and in the case of the work described herein, such measurement is made by utilizing a Corning Blood Gas Analyzer, Model Number 165, manufactured by the Corning Glass Company of New York.

The Index is determined hourly by recording the value of the current, as read from instrument 22 and contemporaneously withdrawing a sample from the liquid stream by way of the sample hub in the sensor. The sample is then analyzed by the Blood Gas Analyzer and the ratio of the measured current to the actual partial pressure of oxygen is calculated. This value is normalized by multiplying by 100 and the resulting number is the Index as plotted versus time in FIG. 3. Since it is known that the current is directly proportional to the oxygen gas concentration, ideally the Index for a sensor which is measuring a stream of constant oxygen concentration should be constant. The variation of the Index with time from a constant concentration is therefore a measure of the instability of the sensor.

The in vitro testing of performance of the sensors is carried out by measuring the oxygen content in a closed loop stream of oxygenated Hemostrate ® liquid. (Hemostrate ® is a trademark of McGaw Labs of Irvine, Calif.). Hemostrate ® liquid is an aqueous electrolytic solution having the following composition of salts per liter of water.

| Component | Parts by Weight |
|---|---|
| Sodium Chloride | 194 |
| Sodium Acetate | 167 |
| Calcium Chloride 2H$_2$O | 6.4 |
| Magnesium Chloride 6H$_2$O | 5.3 |
| Potassium Chloride | 5.2 |

The Hemostrate ® liquid is diluted with pure water to a dilution ratio of 35 to 1, by volume, and is continuously oxygenated with room air and maintained at body temperature as it is circulated in the closed loop during in vitro testing.

Referring now to FIG. 3, as expected, the Index versus time plot of sensors heretofore employed reaches stable conditions in measuring the constant oxygen concentration Hemostrate ® stream and the Index maintains a constant value throughout the test. This is illustrated in FIG. 3 by the curve labeled IN VITRO (control).

Following in vitro testing, the same sensor is tested in vivo by placing the electrode into an artery of a living dog. The dog is prepared by having food withheld for a period of twelve hours and having been given a pre-anesthetic dose of Acepromazine fifteen to twenty minutes prior to the procedure. The animal is anesthetized with sodium pentabarbital, intubated with a cuffed endotracheal tube and ventilated with a Harvard apparatus ventilator. Aseptically, bilateral femoral, bracheal and carotid arteries are isolated with silk ties placed around the arteries. The electrodes are placed in each of the arteries via arteriotomy and advanced to the central aorta. Arterial bleeding is controlled by the silk ties. Immediately after insertion of each electrode, heparinized Normal Saline is perfused through the sampling lumen at a rate of 2 cc per hour for the duration of the procedure to keep the lumen patent. Hourly readings of current registered on instrument 22 and samples of blood for analysis via the Corning Blood Gas Analyzer are taken to complete the plot of Index versus time.

Referring again to FIG. 3, and specifically, the curve labeled IN VIVO (untreated), it is seen that, in contrast to the in vitro test, wherein stability was reached almost instantaneously, a long time period elapses before the Index value is relatively constant. This surprising result has been found to be typical of prior sensing devices employed in measuring blood gas. As can be seen, the curve of Index versus time is exponential wherein the negative slope is initially high and then decreases until a relatively low negative slope, i.e., stable operation, is realized. Mathematically, the data may be fitted to the function $$I = I_0 e^{-at} + b$$

wherein I is the index, Io, a, and b are constants and t is the time. Stability is defined as the point in time at which the slope has decreased to less than a 5% change in the value of the Index at that time or, mathematically, when:

$$\frac{d(I)/d(t)}{I} \times 100 < 5$$

It has been experienced that once this degree of stability is reached, a doctor can rely on the measurement to indicate a significant change in blood gas concentration. For the prior sensor performance plotted in FIG. 3, it is noted that in general the time to reach such stability, $T_s$, does not occur until 4 to 7 hours have passed. This time is generally intolerable for use of the sensor in many medical procedures.

In accordance with the teachings of this invention, it has now been discovered that this time may be drastically reduced and stability reached within a tolerable time period by subjecting the sensing electrode to a pretreatment which comprises applying to the membrane of the electrode an aqueous solution comprising blood derived albumin.

By the term pretreatment it is meant a treatment of the electrode which is completed in vitro and prior to the insertion of the electrode into a blood stream. Advantageously such pretreatment may be carried out by simply immersing the proximal end of the electrode in the albumin containing solution for a period of time. While some improvement in response time is noted for short pretreatment immersion, e.g., 10 minutes, the time of immersion should be at least 1.0 hours and preferably at least 1.5 hours. The immersion is preferably carried out at an elevated temperature, e.g., between 25° C. and the temperature at which the albumin will tend to degrade, and preferably at temperatures near body temperature, i.e., from about 35° to about 40° C.

Subsequent to immersion, the pretreated electrode may be used directly in the blood vessel of a living animal. Preferably however, the electrode is air dried and then coated with a medical grade Silicone oil which tends to preserve the pretreatment and facilitate the immersion of the electrode into a living animal. The silicone coated electrode may be sterilized using such conventional sterilizing means as ethylene oxide sterilization, all without effecting the advantageous results of the pretreatment.

A wide variety of blood derived albumin containing solution may be employed for use in the pretreatment step of this invention. For example, albumin, in the form of a freeze dried powder is commercially available and may be obtained in purities of 99%, by weight, of protein and 98%, by weight, of pure albumin. These powders are generally free of fatty acids, containing less than 0.1 moles of fatty acid per mole of albumin, and may be employed in an aqueous solution for the pretreatment of this invention.

Also available are protein fractions from human blood which consist primarily of albumin with small amounts of heat stable alpha- and beta- globulins.

The preferred blood derived albumin containing solution for use in this invention, is human serum, i.e., the pale yellow liquid squeezed out of clotted whole blood. Human serum is approximately 92% by weight water, 7% protein, less than 1% by weight of various salts and approximately 0.1% by weight glucose. The inorganic components, other than water, include chloride, sodium, bicarbonate, potassium, phosphate, calcium, silicon, sulfur, magnesium, zinc, copper or iron ions. Carbohydrates other than glucose may be found including pentose and other polysaccharides. Additionally, non-protein nitrogen compounds such as amino acids, creatine, creatinine, uric acid and urea are present. Certain lipids such as fatty acids, e.g., stearic acid, fats, cholesterol and phospholipids are present. Among the proteins, the predominant component is albumin with significant quantities of alpha-, beta-, and gamma-globulin also present. Additionally, the protein fibrinogen is present. Needless to say, such serum is carefully screened to insure that it is obtained from a healthy human and that it is free of hepatitis infection microbes. In the case of use of the pretreated sensor in new born children, it is also advisable to screen for Cytomegalovirus (CMV) as most healthy adult human blood is usually so contaminated.

Referring again to FIG. 3, and specifically the curve labeled IN VIVO (treated), plotted there is the performance of a typically pretreated electrode in vivo use. The pretreatment comprised immersion in human blood serum for a period of two hours. As is evident from this plot, the sensor reached stability almost instantaneously and throughout the procedure continued to operate within a stability of 5%, as defined above.

EXAMPLE 1

A series of sensors are manufactured having the construction illustrated in FIGS. 1 and 2. Each of the sensors employ a polyvinyl chloride bilumen tube measuring 1.35 mm in diameter and utilize a silver electrode having a cross sectional diameter of 0.15 mm. The electrode is encased at its proximal end in epoxy resin and is covered by a membrane comprising cross linked polyhydroxyethyl methacrylate. The thickness of the membrane measured from the top of the silver electrode is 0.015 mm. A water bath is prepared and maintained at 37°±2° C. A quantity of sterilized human blood serum taken from a donor screened for Hepatitis B surface Antigen and for Cytomegalovirus is placed in a beaker which is placed into the water bath to maintain a constant temperature. The serum in the beaker is under constant gentle agitation. The tip of the electrode is immersed into the serum to a depth of 0.5 cm and held immersed for 120±10 minutes. The electrode is then removed and USP sterile water is used to flush the sampling lumen free of any serum. The electrode is then placed on absorbent towelling and air dried using a drying rack for 1 to 2 minutes. The electrode tubing is then wiped and medical grade silicone fluid (MG360 Silcone fluid obtained from the Dow Corning Company of Midland, Mich.) is dabbed onto the tip to maintain uniform but light coverage of the surface. The tubing is then packaged along with the other components of the sensor (as illustrated in FIG. 1) and then subjected to ethylene oxide sterilization.

EXAMPLE 2

The procedure of Example 1 is carried out with the exception that a human blood plasma protein fraction is substituted for the blood serum. This fraction is sold by the Hyland Therapeutics Division of Traverol Laboratories, Inc. of Glendale, Calif. under the trademark Protenate Plasma Protein Fraction and comprises primarily albumin with small amounts of heat stable alpha- and beta-globulins in a 5% aqueous solution.

EXAMPLE 3

The procedure of Example 1 is carried out with the exception that an aqueous solution of human blood derived albumin freeze dried powder is employed, the solution containing 30% by weight of the albumin powder. The powder is obtained from Miles Laboratories, Inc. of Elkhart, Ind. and is sold by them as Human Albumin Fatty Acid Free Code No. 82-323. The powder is 99% protein, 98% albumin and contains less than 0.1 moles of fatty acid per mole of albumin.

COMPARATIVE EXAMPLE 1

The procedure of Example 1 is carried out with the exception that a 30% by weight aqueous solution of dextran is employed. Dextran is a high molecular weight polymer of D-glucopyranose synthesized from sucrose by bacterial species of the family lactobacillus. The dextran employed is sold by Pharmacia Fine Chemicals of Piscataway, N.J. as Dextran T500 and has an average molecular weight of approximately 500,000 and a limiting viscosity number (20° C.) of approximately 0.53.

COMPARATIVE EXAMPLE 2

The procedure of Example 1 is carried out with the exception that the steps of immersing the electrode in a solution and drying is eliminated, i.e., no pretreatment.

TEST RESULT

Figure 4:
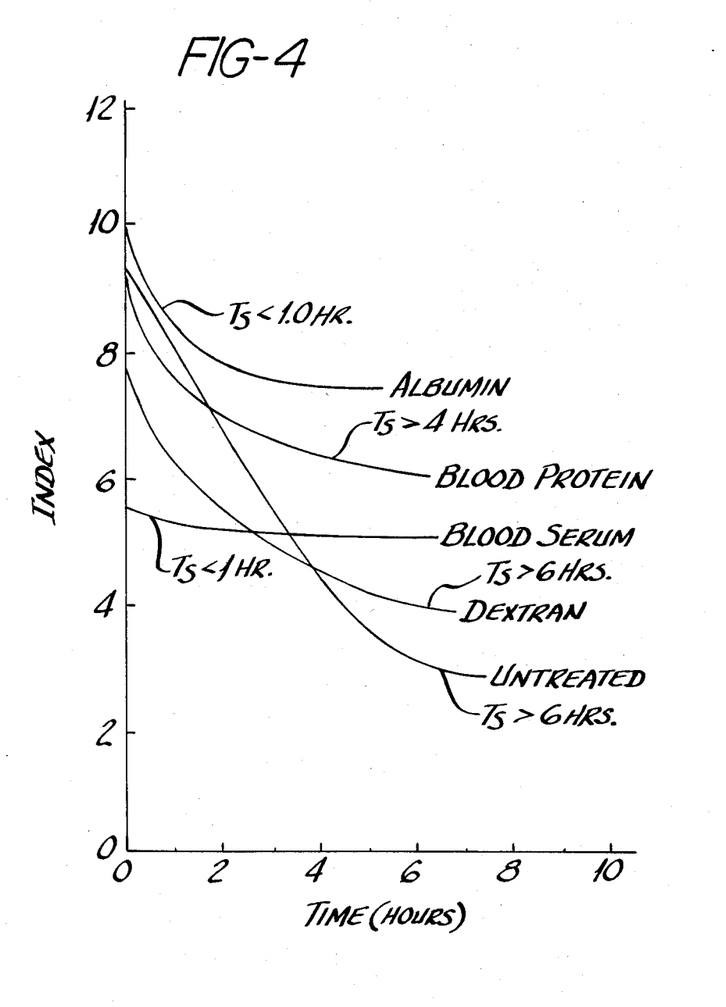
FIG. 4 is a graphical representation of the stabilization time of electrodes treated in various solutions as well as that of an untreated electrode.

Each of the electrodes of the foregoing examples are tested in vivo in dogs utilizing the testing procedure set out above in connection with the description of FIG. 3. The results of these tests are summarized in Table 1 below and graphically represented in FIG. 4.

TABLE 1

| Example | Pretreatment | Stability Time |
| --- | --- | --- |
| Ex. 1 | Blood Serum | 0–1 hrs. |
| Ex. 2 | Blood Protein | 3–4 hrs. |
| Ex. 3 | Albumin | 0–1 hrs. |
| Comp. Ex. 1 | Dextran | >6 hrs. |
| Comp. Ex. 2 | Untreated | >6 hrs. |

As can be seen from the above, the stability time, as defined herein, for the untreated sample was greater than 6 hours, an intolerably long period. Likewise the use of dextran produces no improvement. Each of the blood derived albumin containing solutions, when employed to pretreat, produced a substantial improvement with blood serum being particularly effective.

What is claimed is:

1. In an electrode assembly for insertion into a living animal to continuously monitor blood gas concentration, which assembly includes an electrode and a hydrophilic polymer membrane covering said electrode, wherein said membrane is hydrophilic substantially throughout its thickness, the improvement which comprises:

said covering membrane being pretreated by having applied thereto a liquid solution comprising blood derived albumin, said pretreated membrane than being sterilized; and said electrode assembly exhibiting a lower $T_S$ than an assembly having an untreated membrane.

2. The electrode assembly of claim 1 wherein the $T_S$ is less than six hours.

3. The electrode assembly of claim 1 wherein said liquid solution is an aqueous solution.

4. The electrode assembly of claim 1 wherein said liquid solution is a solution of essembly pure blood derived albumin.

5. The electrode assembly of claim 4 wherein said blood derived albumin is human blood derived albumin.

6. The electrode assembly of claim 1 wherein said liguid solution is a solution of blood derived proteins.

7. The electrode assembly of claim 6 wherein said blood derived proteins are human blood derived proteins.

8. The electrode assembly of claim 1 wherein said liquid solution is blood serum.

9. The electrode assembly of claim 8 wherein said blood serum is human blood serum.

10. A method for decreasing the $T_S$ of an electrode assembly for insertion in a living animal to continuously monitor blood gas concentration, which assembly includes an electrode and a hydrophilic polymer membrane covering said electrode, wherein said membrane is hydrophilic substantially throughout its thickness, comprising the steps:

pretreating said electrode by applying to said membrane a liquid solution comprising blood derived albumin and then sterilizing said electrode, whereby the $T_S$ of said electrode assembly is substantially lower than an assembly having an untreated membrane.

11. The method of claim 10 wherein said liquid is applied by immersing said electrode in said liquid for at least 10 minutes.

12. The method of claim 11 wherein said electrode is immersed in said liquid for at least one hour.

13. The method of claim 10 wherein said electrode is dried after said solution is applied.

14. The method of claim 13 wherein said electrode is sterilized after it is dried.

15. The method of claim 13 wherein silicone is applied to said electrode prior to drying.

* * * * *

UNITED STATES PATENT AND TRADEMARK OFFICE
CERTIFICATE OF CORRECTION

PATENT NO. : 4,499,901

DATED : Feb. 19, 1985

INVENTOR(S) : Chang et al.

It is certified that error appears in the above—identified patent and that said Letters Patent is hereby corrected as shown below:

On the title page;

The title for this patent should read "Pretreated Sensing Electrode"

In column 9, line 4, claim 4, "essembly" should read "essentially"

In column 9, line 9, claim 6, "liguid" should read "liquid"

Signed and Sealed this

Thirteenth Day of August 1985

[SEAL]

Attest:

DONALD J. QUIGG

Attesting Officer — Acting Commissioner of Patents and Trademarks